(12) United States Patent
Callahan et al.

(10) Patent No.: US 6,324,423 B1
(45) Date of Patent: Nov. 27, 2001

(54) QUANTITATIVE METHOD AND APPARATUS FOR MEASURING QT INTERVALS FROM AMBULATORY ELECTROCARDIOGRAPHIC RECORDINGS

(76) Inventors: Timothy Callahan; William Shell, both of 2980 Beverly Glen Cir., Suite 300, Los Angeles, CA (US) 90077

( * ) Notice: Subject to any disclaimer, the term of this patent is extended or adjusted under 35 U.S.C. 154(b) by 0 days.

(21) Appl. No.: 09/292,995

(22) Filed: Apr. 16, 1999

Related U.S. Application Data

(60) Provisional application No. 60/082,246, filed on Apr. 17, 1998.

(51) Int. Cl.$^7$ ................................................. A61B 5/0452
(52) U.S. Cl. ................................................. 600/516
(58) Field of Search ...................... 600/509, 516, 600/515, 519, 521

(56) References Cited

U.S. PATENT DOCUMENTS

| | | |
|---|---|---|
| 4,417,306 * | 11/1983 | Citron et al. . |
| 5,419,338 | 5/1995 | Sarma et al. . |
| 5,437,285 | 8/1995 | Verrier et al. . |
| 5,560,368 | 10/1996 | Berger . |
| 5,560,370 | 10/1996 | Verrier et al. . |
| 6,132,381 * | 10/2000 | Forbes et al. . |

OTHER PUBLICATIONS

Algra et al., QTc Prolongation Measured By Standard 12–Lead Electrocardiography Is an Independent Risk Factor for Sudden Death Due To Cardiac Arrest. Circulation (1991) 83:1888–94.

Schwartz et al., QT Interval Prolongation as Predictor of Sudden Death In Patients With Myocardial Infarction. Circulation (1978) 57:1074–77.

Sawicki et al., Prolonged QT interval as a predictor of mortality in diabetic nephropathy. Diabetologia (1996) 39:77–81.

Schwartz et al., Fundamentals of clinical cardiology—The long Q–T syndrome. American Heart Journal 89, No. 3:378–90 (1975).

Garson, How to Measure the QT Interval—What Is Normal? Am J Cardiol (1993); 72:14B–16B.

Bazett, An Analysis Of The Time–Relations Of Electrocardiograms. Heart (1920); 7:353–70.

Karjalainen et al., Relation Between QT Intervals and Heart Rates From 40 to 120 beats/min in Rest Electrocardiograms of Men and a Simple Method to Adjust QT Interval Values. JACC (1994); vol. 23. No. 7, 1547–53.

Coumel et al., Clinical Relevance of Assessing QT Dynamicity in Holter Recordings. Journal Of Electrocardiology, vol. 27 Supplement, 62–66.

Cappato et al., Sympathetic and Vagal Influences on Rate–Dependent Changes of QT Interval in Healthy Subjects. Am J Cardiol (1991); 68:1188–93.

Browne et al., Influence of the Autonomic Nervous System on the Q–T Interval in Man. Am J Cardiol (1982); 50:1099–1103.

(List continued on next page.)

Primary Examiner—Scott M. Getzow
(74) Attorney, Agent, or Firm—Lyon & Lyon LLP

(57) ABSTRACT

A quantitative method and apparatus for measuring a cardiac function interval. Beat-to-beat data representative of a cardiac interval is collected over an extended period of time. A series of bins, each of which has a defined value range, is defined. The collected data is organized into the bins in accordance with the value of the data and the value range of the bin. The percentage of data in each bin may be calculated based upon the quantity of data in each bin.

15 Claims, 16 Drawing Sheets

QTa = QTa interval
Pb = P beginning (or onset)
Pe = P end
Te = T end
Rp = Repeat

OTHER PUBLICATIONS

Kautzner et al., The Effects of Reflex Parasympathetic Stimulation on the QT Interval and QT Dispersion. Am J Cardiol (1997); 80:1229–32.

Molnar et al., Diurnal Pattern of QTc Interval: How Long is Prolonged? Possible Relation to Circadian Triggers of Cardiovascular Events. J Am Coll Cardiol (1996); 27:76–83.

Berger et al., Beat–to–Beat QT Interval Variability: Novel Evidence for Repolarization Lability in Ischemic and Nonischemic Dilated Cardiomyopathy. Circulation (1997) 96:1557–65.

Morganroth et al., Variability of the QT Measurement in Healthy Men, with Implications for Selection of an Abnormal QT Value to Predict Drug Toxicity and Proarrhythmia. Am J Cardiol (1991); 67:774–76.

Molnar et al., Evaluation of Five QT Correction Formulas Using a Software–Assisted Method of Continuous QT Measurement from 24–Hour Holter Recordings. Am J Cardiol (1996); 78:920–26.

Funck–Brentano et al, Rate–Corrected QT Interval: Techniques and Limitations. Am J Cardiol (1993); 72:16B–22B.

* cited by examiner $$\%QT = \sum_{i=1}^{n} \frac{(QTi)}{N}$$

$$\%QTc = \sum_{i=1}^{n} \frac{(QTci)}{N}$$

QTa = QTa interval
Pb = P beginning (or onset)
Pe = P end
Te = T end
Rp = Repeat

QUANTITATIVE METHOD AND APPARATUS FOR MEASURING QT INTERVALS FROM AMBULATORY ELECTROCARDIOGRAPHIC RECORDINGS

This application claims benefit of Provsional No. 60/082,246, filed Apr. 17, 1998.

FIELD OF THE INVENTION

The present invention relates to measuring cardiac function intervals.

BACKGROUND OF THE INVENTION

It is known that prolongation of the QT interval may be a marker for sudden death. Measurements of the QT interval are generally taken from a 12-lead electrocardiogram. The 12-lead electrocardiogram provides only point-in-time data, thus missing the beat-to-beat dynamicity data available from a Holter recording. Heretofore, beat-to-beat data has been averaged due primarily to constraints in computing power. Unfortunately, averaging minimizes the understanding of the beat-to-beat variability inherent in QT interval data.

Increases in the QT and QTc intervals of a 12-lead Electrocardiogram (ECG) are associated with an increased risk of cardiac dysrhythmias and sudden cardiac death. See, for example, Algra A, Tijssen J G P, Roelandt R T C, Pool J, Lubsen J: QTc Prolongation measured by standard 12-lead electrocardiography is an independent risk factor for sudden death due to cardiac arrest. Circulation 83:1888, 1991; Schwartz P J, Wolf S: QT interval prolongation as predictor of sudden death in patients with myocardial infarction. Circulation 57:1074, 1978; Sawicki P T, Dahne R, Bender R, Berger M: Prolonged QT interval as a predictor of mortality in diabetic neuropathy. Diabetologia 39:77, 1996.

While the resting 12-lead electrocardiogram may provide important spacial information regarding the status of ventricular repolarization, the use of a single 12-lead ECG measured randomly in time may disregard potentially important prognostic data regarding the dynamicity, temporal relationships, and circadian rhythms of the QT interval.

It is known that the QT and QTc intervals may undergo significant changes over both the shorter and longer term due to circadian rhythms. See, for example, Yi G, Guo X, Reardon M, Gallagher M M, Hnatkova K, Camm A J, Malik M: Circadian variation of the QT interval in patients with sudden cardiac death after myocardial infarction. Am J Cardiol 81:950, 1998.

It is known that the QT and QTc intervals may undergo significant changes over both the shorter and longer term due to autonomic control. See, for example, Cappatto R, Alboni P, Pedroni P, Gilli G, Antoniolli G: Sympathetic and vagal influences on rate-dependent changes of QT interval in healthy subjects. Am J Cardiol 68:1188, 1991; Browne K F, Zipes D P, Heger J J, Prystowsky E N: Influence of the autonomic nervous system on the Q-T interval in man. Am J Cardiol 50:1099, 1982; Kautzner J, Hartikainen J E K, Heald S, Camm A J, Malik M: The effects of reflex parasympathetic stimulation on the QT interval and QT dispersion. Am J Cardiol 80:1229, 1997.

A single 12-lead ECG taken at a given point in time may provide misleading and inaccurate cardiac risk data. Therefore, analysis of the QT interval for an entire 24-hour period may provide additional information regarding the risk of sudden death not available on the single, random 12-lead ECG.

Recently, it has become possible to measure the QT interval on 24-hour Holter (AECG) recordings. These measurements have generally been reported as averages over short time periods, typically between about 15 seconds and about five minutes. See, for example, Molnar J, Zhang F, Weiss J, Ehlert F A, Rosenthal J E: Diurnal Pattern of QTc Interval: How long is prolonged? Possible relation to circadian triggers of cardiovascular events. J Am Coil Card 27:76, 1996; Yanaga T, Maruyama T, Kumanomido A, Adachi M, Noguchi S, Taguchi J: Usefulness of automatic measurement of QT interval using Holter tape in patients with hyperthyroidism. J Am Monit 6:27, 1993.

More recently beat-to-beat QT interval measurements have been used. The use of averaged QT measurements may obscure significant short-term variations in the QT intervals. Conversely, beat-to-beat measurements retain the natural variability data that may be important for calculating a patient's risk of dysrhythmia and sudden death.

Although beat-to-beat variability of the QT interval has been described by Berger and others (see Berger R D, Kasper E K, Baughman K L, Marban E, Calkins H, Tomaselli G F: Beat-to-beat QT interval variability: Novel evidence for repolarization lability in ischemic and nonischemic dilated cardiomyopathy. Circulation 96:1557, 1997), little is known regarding normal ranges in variability and measures of the QT interval over a 24-hour period using beat-to-beat measurements.

Molnar and colleagues published a study that gives some indication of the dynamic range of the QT intervals. They reported a mean maximum QTc interval of 495 ms for normal subjects using 24-hour ambulatory monitoring. They also showed a mean intra-subject change of 95 ms. Molnar further reported six normal female subjects as having a maximum mean QTc interval measurement of more than 500 ms. These mean maximum measures were taken over a five minute period. They did not report on the number of beats with a QTc that exceeded 0.45 seconds.

Morganroth and colleagues, using a manual analysis of Holter ECG recordings, found that most normal subjects had QTc intervals of greater then 0.45 seconds at some period during the 24-hour recording. See Morganroth J, Brozovich F V, McDonald J T, Jacobs R A: Variability of the QT measurement in healthy men, with implications for selection of an abnormal QT value to predict drug toxicity and proarrhythmia. Am J Cardiol 67:774, 1991.

The use of mean QTc measurements tends to obscure the individual beats that may exceed traditional normal values for QT and QTc. While traditional measurements, such as measures of central tendency, have been used extensively to describe the relationship of QT and QTc measurements to a so-called normal value, these measurements tend to ignore temporal dynamicity inherent in cardiac function. These measurements may be important to give an overall picture of the status of the subject, however.

It has long been recognized that prolongation of the QT interval may be related to sudden death in a variety of clinical syndromes. The exact relationship, however, has been difficult to define, partly because the QT interval is a dynamic measurement and changes have been observed in both the shorter term (beat-to-beat) and in the longer term (circadian rhythm).

A consistent manual measurement of the QT interval on the resting 12-lead ECG can be imprecise and non-reproducible. Savelieva et al. showed that there was a high degree of variability when using hand-measurements of the QT interval on the 12-lead ECG. See Savelieva I, Yi G, Guo X, Hnatkova K, Malik M: Agreement and reproducibility of automatic versus manual measurement of QT interval and QT dispersion. Am J Cardiol 81:471, 1998. Applicants agree with the conclusions of Savelieva and colleagues that automated measurements offer a higher degree of consistency and reliability than manual measurements.

Traditionally, the QT interval has been measured on a resting 12-lead ECG. In general, this method involves a manual estimation of the onset of the Q-wave and determination of the end of the T-wave. Several beats are used to determine the QT interval. One advantage of measuring the QT interval on a resting 12-lead ECG is that lead placement is generally consistent and a full range of electrocardiographic frequencies may be available for measurement.

One disadvantage of measuring the QT interval on a resting 12-lead ECG is related to the short observation period. The QT interval may be subject to dynamic change on both a beat-to-beat basis and over time, particularly displaying changes in circadian rhythm and in response to alteration of autonomic function. Accordingly, a 12-lead ECG may not reflect the true state of the QT interval, but only a representation at a single point in time.

Up to now, a method to measure the beat-to-beat variation of the QT interval on 24-hour AECG tapes has been unavailable. Most previous studies have focused on average QT interval measurements over several seconds or minutes, rather than individual beat-to-beat measurements.

There have been several attempts to measure the QT interval on 24-hour AECG recordings using a variety of Holter analysis systems. The sampling rate of these Holter analyzers has varied from about 125 Hz to about 200 Hz, at both 8 bit and 12-bit resolution. In addition, these systems have used averages of both RR and QT intervals to overcome data-processing problems. These averages have ranged from about 6 seconds to about 5 minutes. The use of averages tends to obscure beat-to-beat dynamic changes in QT and QTc intervals. For example, normal subjects have some beats with increased QT and QTc measurements, and subjects with known ILQT may have many normal QT and QTc measurements.

It is an objective of the present invention, in a preferred embodiment, to enable the assessment of the QT and QTc intervals and other cardiac function intervals on a beat-to-beat basis, providing a quantitative index of the percentage of individual beats with QT and QTc intervals.

It is another objective of the present invention, in a preferred embodiment, to enable the measurement and assessment of the QT and QTc intervals and other cardiac function intervals over an extended period of time, including not only periods of time greater than about one minute but also periods of time lasting at least 24 hours and even longer, in some cases.

SUMMARY OF THE INVENTION

In accordance with the present invention, in a preferred embodiment, this and other objectives are achieved by providing a method and apparatus for analyzing beat-to-beat QT intervals from high-resolution Ambulatory Electrocardiographic monitoring (AECG) to detect the percentage of beats in a prolonged AECG recording that exceed a discrete time-based threshold. Beat-to-beat QT and RR intervals may be measured to calculate beat-to-beat QTc. In a preferred embodiment, the percentage of beats in which the QT and QTc intervals exceed 0.45 seconds (%QT and %QTc) may be examined.

The present invention, in a preferred embodiment, provides a method and apparatus to analyze beat-to-beat QT data, stratify the data according to a time-series bin-array, and calculate the percentage of beats that fall outside a predetermined, user-defined threshold. This method and apparatus may be applicable to a wide variety of different subjects including, for example, normal subjects, subjects with long QT syndrome (ILQTS), and drug titration studies.

Further objects, advantages and other features of the present invention will be apparent to those skilled in the art upon reading the disclosure set forth herein.

BRIEF DESCRIPTION OF THE DRAWINGS

A detailed description of a preferred embodiment of the present invention will be made with reference to the accompanying drawings.

DETAILED DESCRIPTION OF THE PREFERRED EMBODIMENTS

Figures 1, 2, 3:
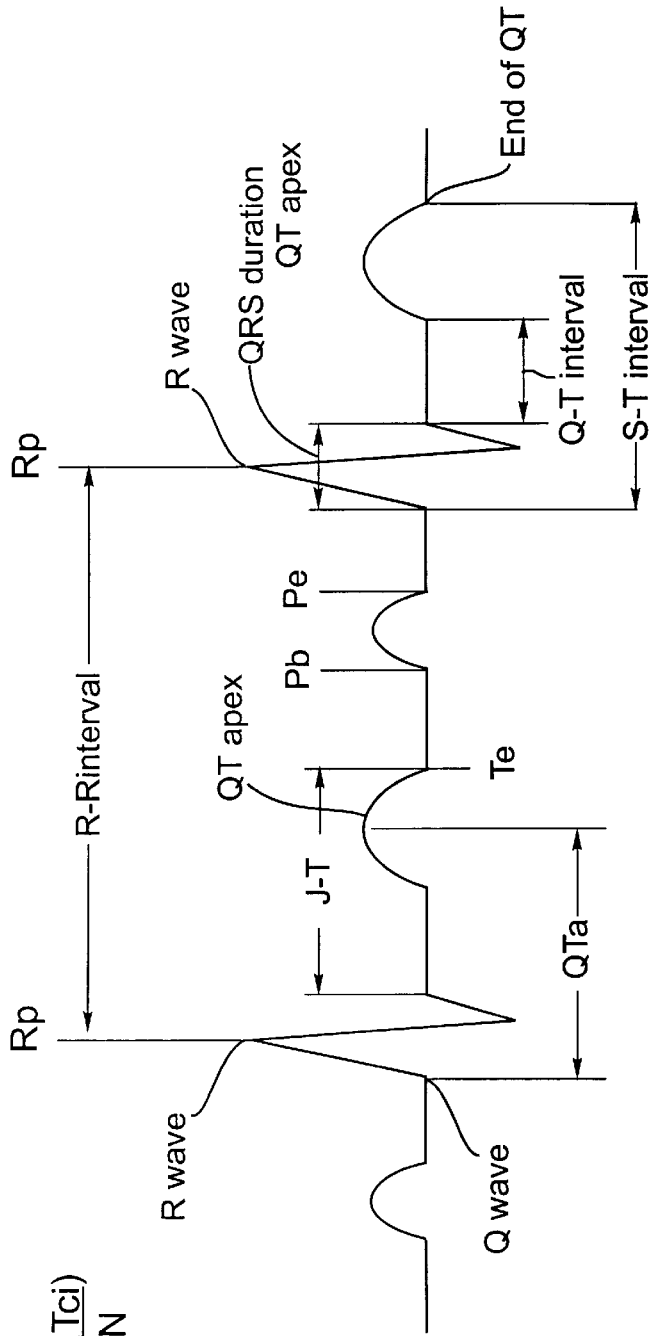
FIG. 1 illustrates an example of a mathematical formula for constructing a bin for calculating a QT index in accordance with one embodiment of the present invention.
FIG. 2 illustrates an example of a mathematical formula for constructing a bin for calculating a QTc index in accordance with one embodiment of the present invention.
FIG. 3 illustrates an example of ECG fiducial points and a computer generated QT interval with a cursor in place.

The following detailed description is of the best presently contemplated mode of carrying out the invention. This description is not to be taken in a limiting sense, but is made merely for the purpose of illustrating the general principles of the invention. The scope of the invention is best defined by the appended claims.

In a preferred embodiment, standard 24-hour AECG recordings may be obtained using either a Del Mar Scientific model 420 (Del Mar Avionics, Irvine, Calif.) or a Reynolds Tracker II (Reynolds Medical, England) recorder, for example. These recorders are commercially available and need not be modified.

Analog signals from the cassette recordings may be digitized at 12-bit resolution using a Reynolds PathFinder 700 Holter analyzer (Reynolds Medical, England) system, for example. The sampling rate of the algorithm may begin at 128 samples per second. For QT interval analysis, the sampling rate may preferably be increased to 128×128 samples per second.

The digitized data may be reconstructed and displayed using a Reynolds PathFinder 700 Holter analyzer on a high-resolution computer monitor. A QT analysis may preferably be started after an arrhythmia analysis has been completed and ectopic beats and artifacts have been excluded.

A QT interval analysis may be accomplished in the following manner: The onset of a Q-wave (Qb) may be defined and a cursor may be placed at this point. The end of a T-wave (Te) may be defined and a second cursor may be placed at this point. The data from the tape may then be replayed at 60-times normal time, while the cursors on the Qb and Te points may be monitored for stability. If either cursor wavers from the Qb or Te points, the cursors may be replaced and the affected portion of the data may be reanalyzed. The QT interval may be defined as the time difference between the time points at Qb and Te. The QT intervals may be measured for the entire AECG recording on a beat-to-beat basis.

The peak of an R-wave may be detected and a third cursor may be placed (Rp). Accordingly, each QT interval may be matched with the preceding R—R interval. For a 24-hour recording, this may result in approximately 100,000 beats for which a QT interval and an R—R interval may be defined. The data may then be output to a high-speed computer for post-analysis processing.

In the examples described herein use was made of one AECG recording from a normal volunteer, an on-treatment (peak-dose) recording from a subject in a drug treatment study, and one recording from an inherited Long QT Syndrome (ILQT) patient. These recordings help to demonstrate the potential effectiveness of a %QT method in accordance with the present invention over simply analyzing the mean QT interval measurement. All subjects were male, less than 60 years old.

In the examples described herein QTc was calculated by removing a time-series of the QT and preceding R—R intervals to a high-speed computer with both a fast processor and adequate disk storage space. For each QT interval, a QTc may be calculated using Bazett's correction formula. This formula may be stated as:

$$QTc = QT(msec)/Sqr(R-R)$$

Calculation of %QT and %QTc may be achieved by first constructing a two-dimensional, time-series array (bin) at about 0.01 second intervals. In a preferred embodiment the bin-array may range from about 0.30 seconds to about 0.70 seconds, with additional bins designed to capture beats with QT or QTc measurements of less than 0.30 seconds or greater than 0.70 seconds.

The QT and QTc intervals may be individually placed in the bins according to their measurement. In a preferred embodiment the bins may be constructed in accordance with the formulas expressed in FIG. 1 and FIG. 2. The percentage of beats in each bin may be calculated by comparing the number of beats in each bin to the overall number of beats used in the analysis. A construction of a %QT system in accordance with this embodiment of the present invention allows for analysis of a variety of upper-limits (threshold points) based on patient population and condition under investigation. In this embodiment a threshold point of about 450 ms was analyzed.

In addition to an overall (24-hour) analysis, data for each AECG recording may also be analyzed by comparing daytime (about 0700 to about 2300) to nighttime (about 2300 to about 0700). Means for QT interval measurements may be calculated for each hour and the beat-to-beat data may be grouped by hour for ease of display. Differences may be compared from day to night using a student's t-test.

A %QT and %QTc may be calculated for each hour. Daytime and nighttime values (circadian variation) may be compared using a student's t-test.

To assess the accuracy (reliability) of computer-generated QT interval detection in accordance with the present invention, an AECG recording may be scanned ten times using a Holter analyzer. The overall mean QT measurement may be calculated for each analysis, as well as the standard error of the ten individual mean measurements.

Validity may be assessed by having two reviewers select 1000 AECG beats from the analysis and measuring the QT intervals by hand. The manual measurements may be compared against each other and against a computer measurement by a student's t-test.

To ensure data quality, a trained technician may visually monitor the stability of the fiducial point of the AECG during analysis. FIG. 3 represents a computer-generated QT interval with cursors in place. In the present invention the visual end of the T-wave may be used in a manner analogous to a manual measurement. A single AECG recording was analyzed 10 times. Table 1 shows the overall means for each analysis and the mean and standard error for the group. The standard error of the ten recordings was 0.1724. Thus the computer-generated QT interval measurements were reproducible reflecting a 0.001% error.

A sample of 1000 beats was selected for manual measurement. These beats were measured by two reviewers and the results correlated between the reviewers' measurements and the automated measurements. The correlation coefficient between the reviewers' observations and the computer-generated values was 0.938. These results are shown in Table 2.

EXAMPLE 1—NORMAL SUBJECT

Figure 4:
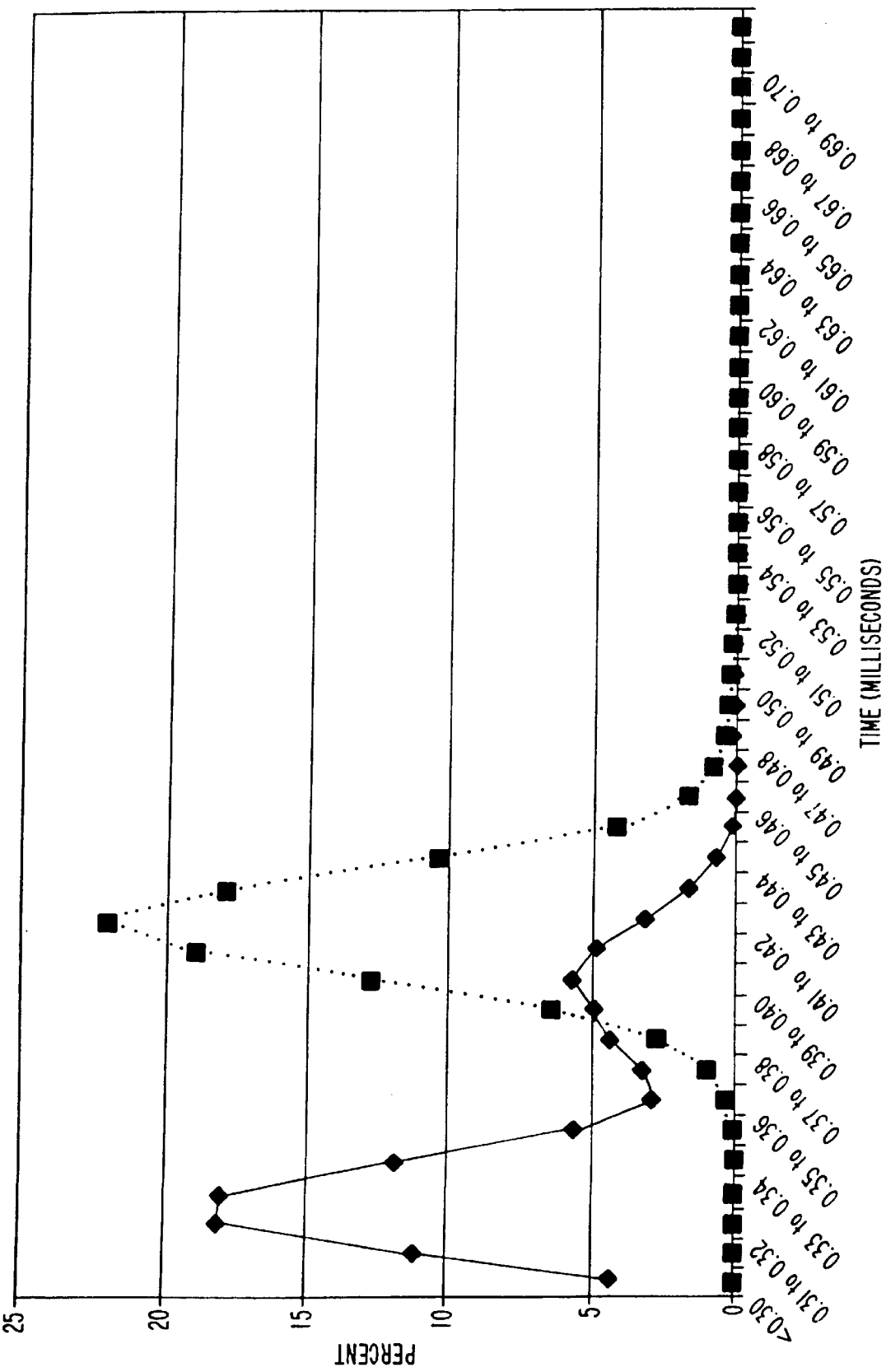
FIG. 4 illustrates an example of a histogram of the %QT and %QTc.

The normal subject had a mean QT interval measurement of 342 ms with a standard deviation of 37 ms. The mean QTc measurement was 414 ms with a standard deviation of 13 ms. Both the mean QT and mean QTc were considered within the normal range (Table 3). When %QT >450 ms was computed, 0.19% (n=173) of the beats had a QT interval measurement of greater than 450 ms and 4.65% (n=4224) of the beats had a QTc measurement of greater than 450 ms. FIG. 4 shows the histogram of the %QT and %QTc for this recording. Thus, 4.65% of the beats recorded on AECG had QTc intervals greater than 450 ms.

When analyzed for circadian differences, a change was seen in the both the mean QT interval and the mean QTc (p<0.001, p<0.001, respectively). Table 4 contains the means and standard deviations of the circadian variation data. More AECG beats at night had QT and QTc intervals greater than 450 ms.

Figure 5:
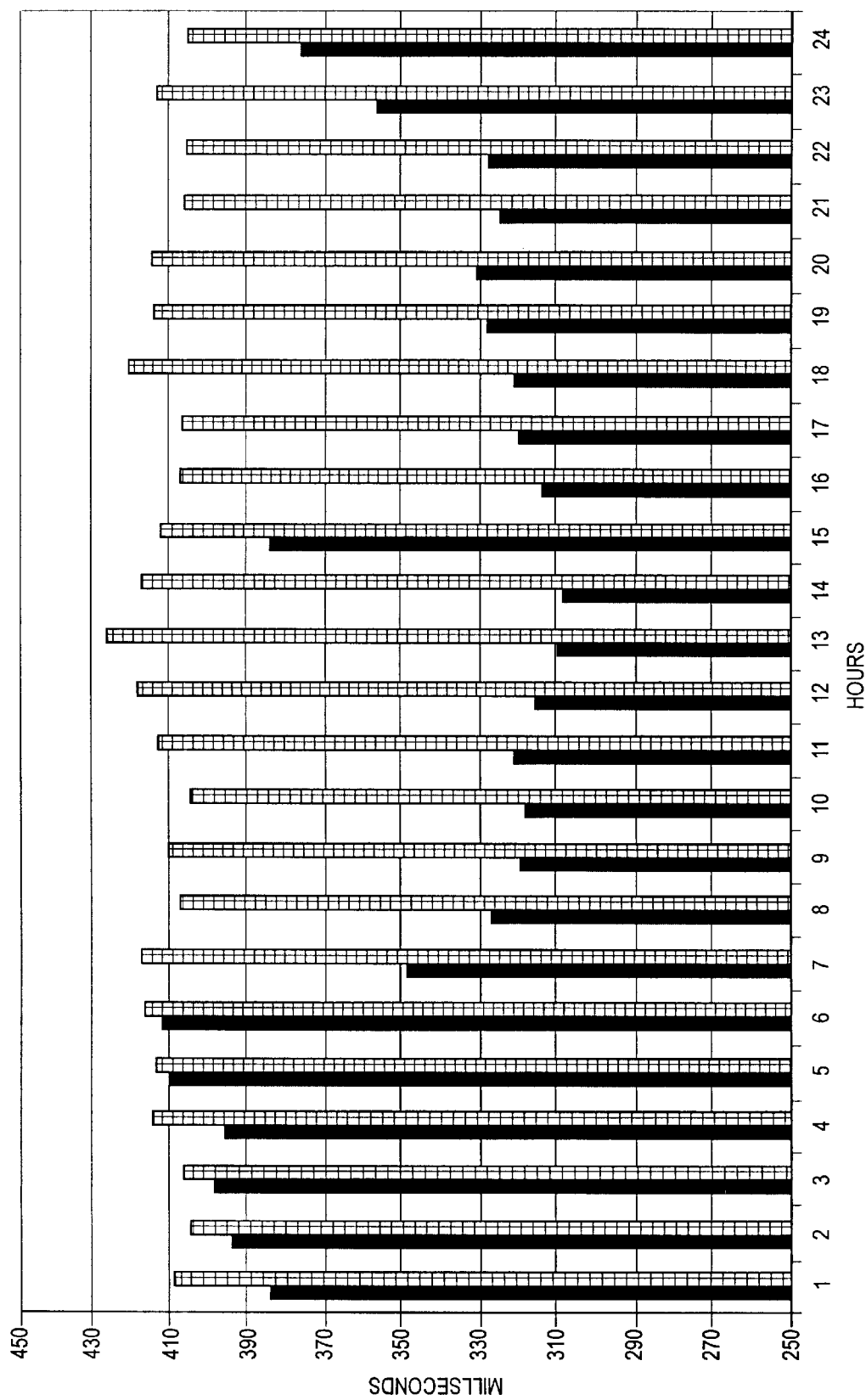
FIG. 5 illustrates an example of hourly calculations for mean QT and QTc for a normal subject (solid=QT, cross-hatched=QTc).
Figure 6:
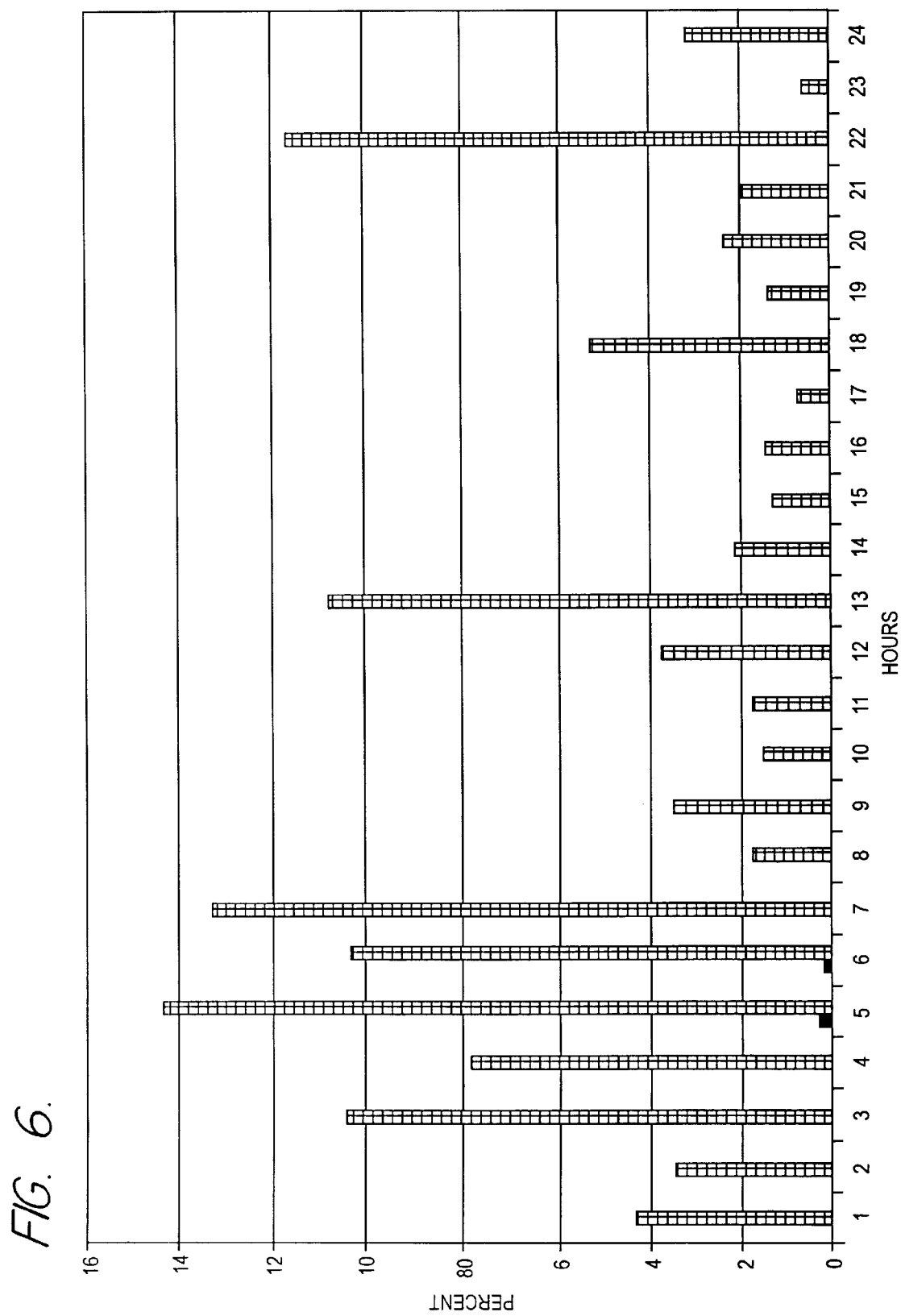
FIG. 6 illustrates an example of hourly %QT and %QTc hour for a Normal Subject

FIG. 5 graphically depicts the hourly calculations for mean QT and QTc, while FIG. 6 graphically depicts the hourly %QT and %QTc.

EXAMPLE 2—DRUG INDUCED PROLONGED QT INTERVAL

One application for a %QT method in accordance with the present invention is to observe the effect of a drug dose on the QT interval measurement. This may be done by comparing the baseline QT interval to the QT interval after dosing.

Figure 7:
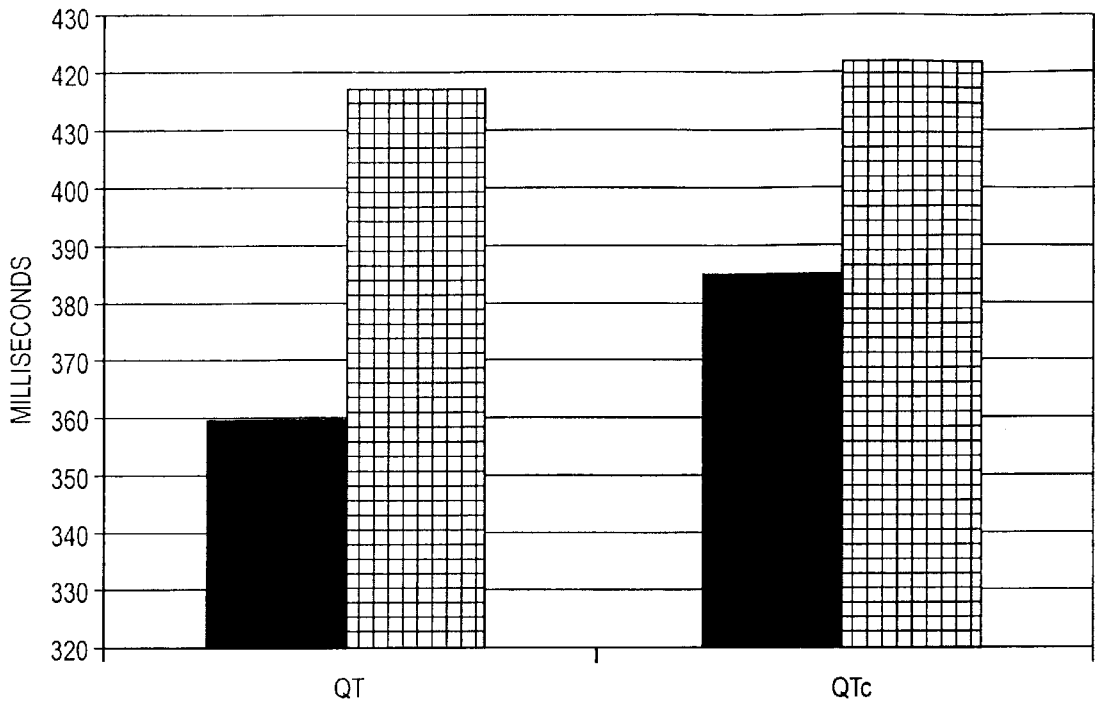
FIG. 7 illustrates an example of an increase in the 24-hour mean QT and QTc from baseline to peak dose (solid=baseline, cross-hatched=Peak Dose)
Figure 8:
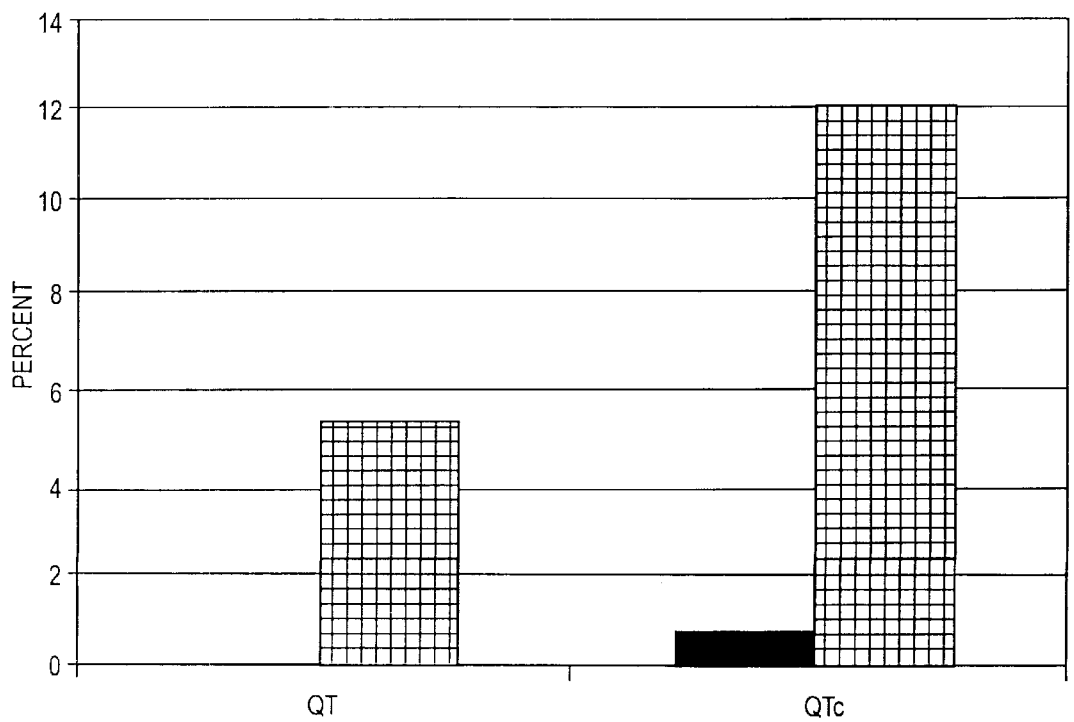
FIG. 8 illustrates an example in which the percentage of beats with %QT and %QTc measurements greater than 450 ms were significantly increased from baseline to peak dose (solid=baseline, cross-hatched=Peak Dose)
Figure 9:
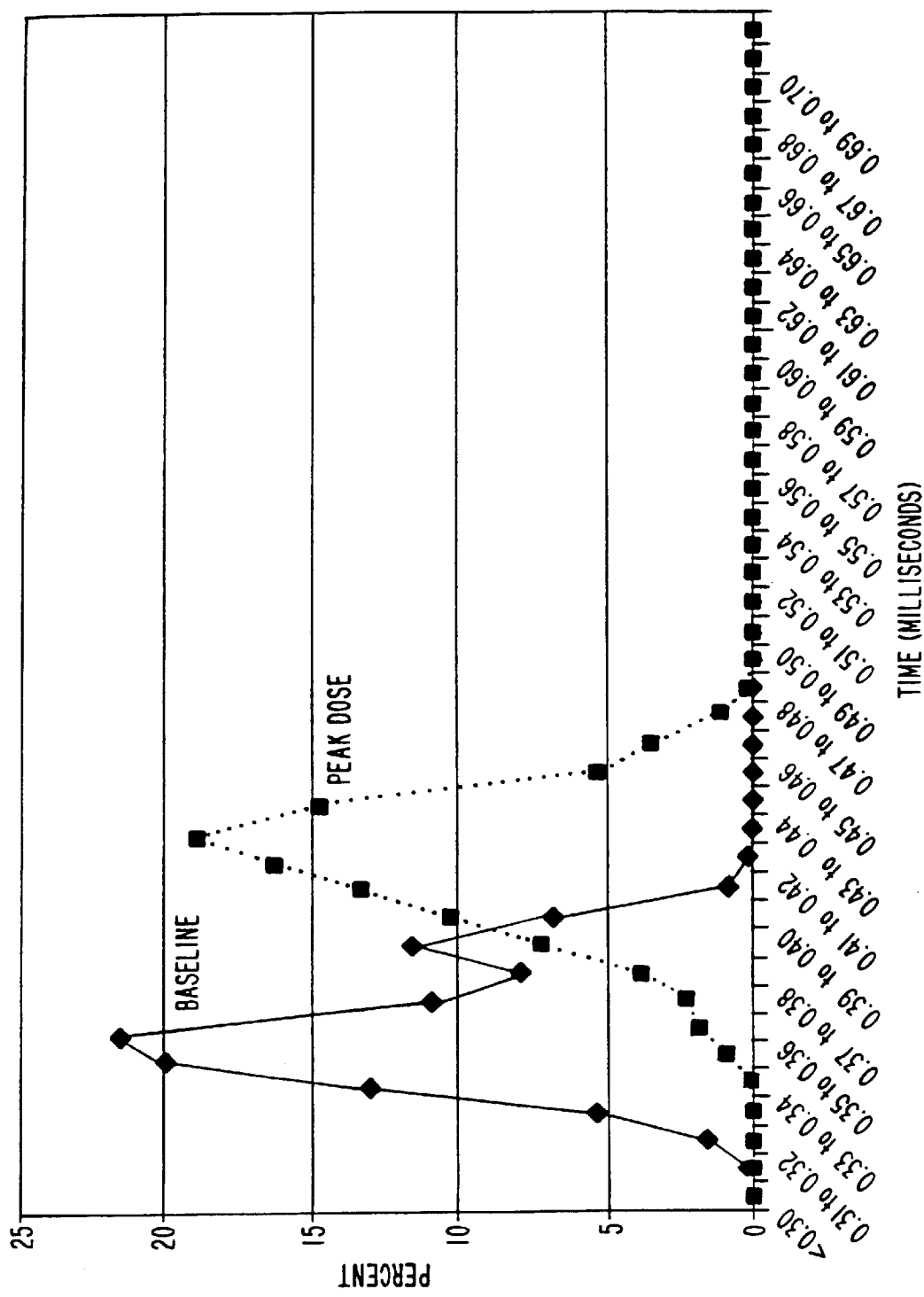
FIG. 9 illustrates an example of a histogram of %QT data from baseline and peak dosing.
Figure 10:
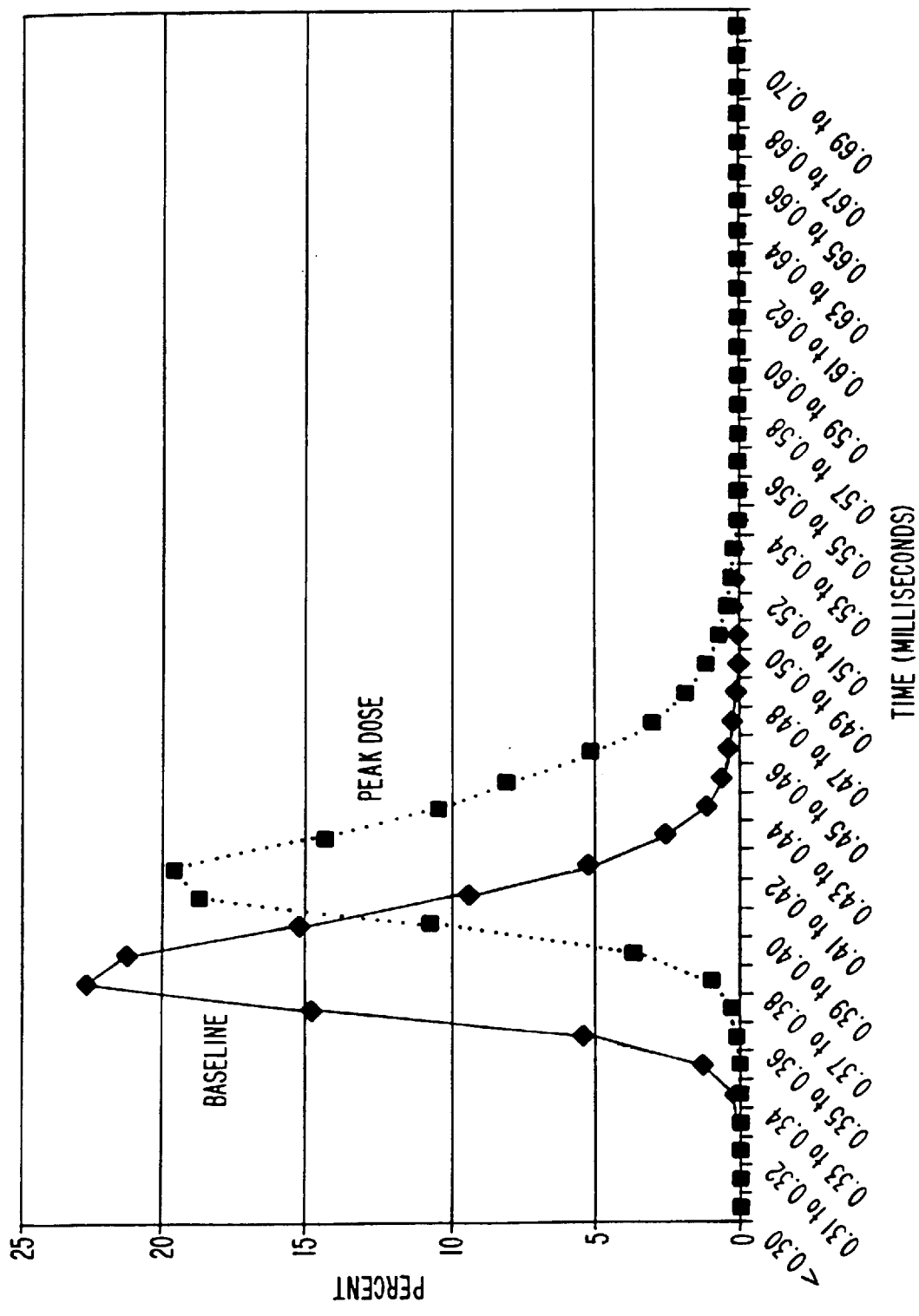
FIG. 10 illustrates an example of a histogram of %QTc data from baseline and peak dosing.

In Example 2 baseline and peak-dose data were taken from a subject in a clinical research trial. The means and standard deviations of the baseline and peak dosing recordings are shown in Table 3. While there was an increase in the 24-hour mean QT and QTc from baseline to peak dose (FIG. 7), both mean QT and QTc were considered normal at the baseline and peak dose. The %QT method shows that the percentage of beats with QT and QTc measurements greater than 450 ms were significantly increased from baseline to peak dose (FIG. 8). A histogram %QT data from baseline and peak dosing is shown in FIG. 9. A histogram %QTc data from baseline and peak dosing is shown in FIG. 10.

Figure 11:
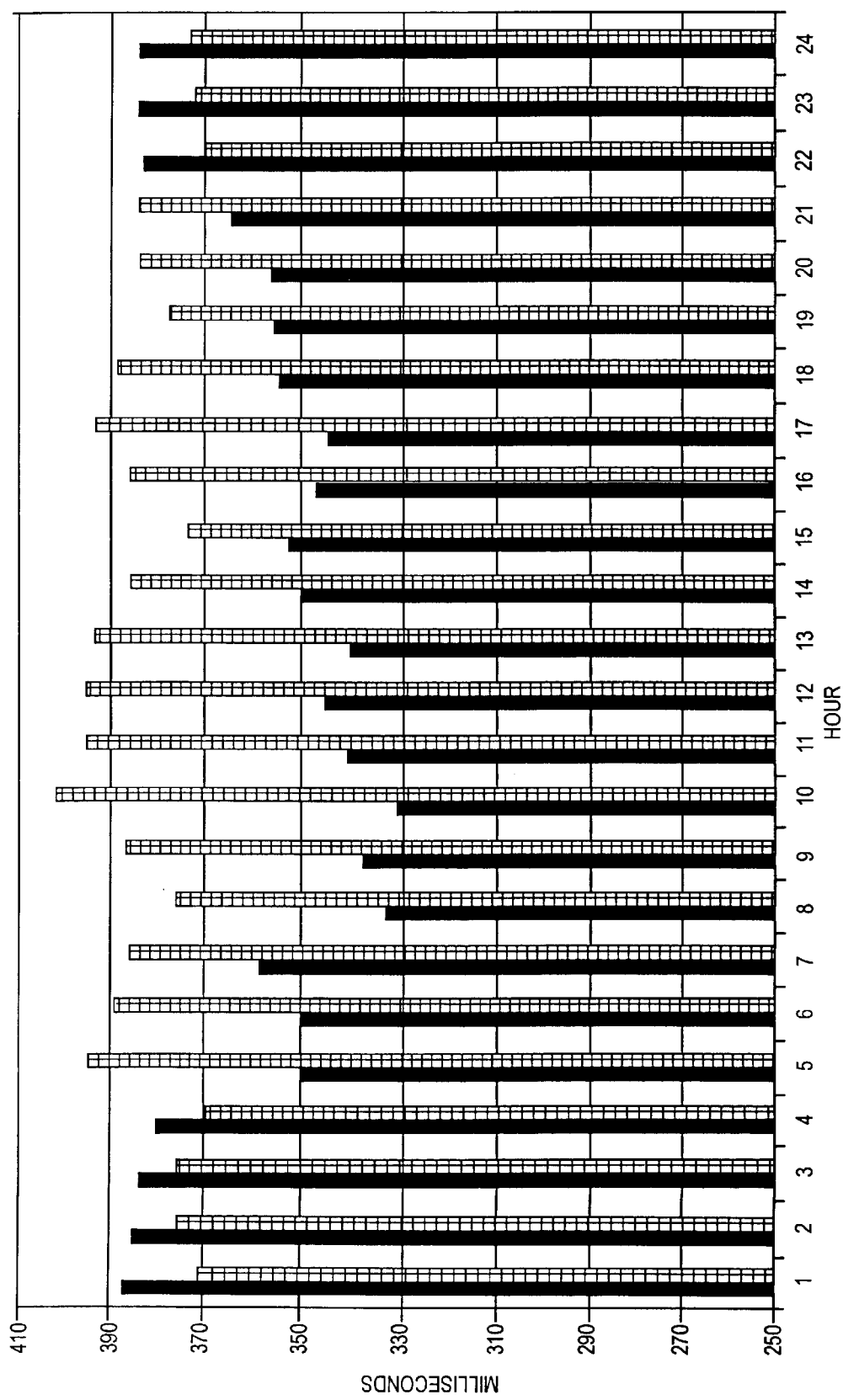
FIG. 11 illustrates an example of average hourly QT and QTc measurements from a baseline recording (solid=QT, cross-hatched=QTc)
Figure 12:
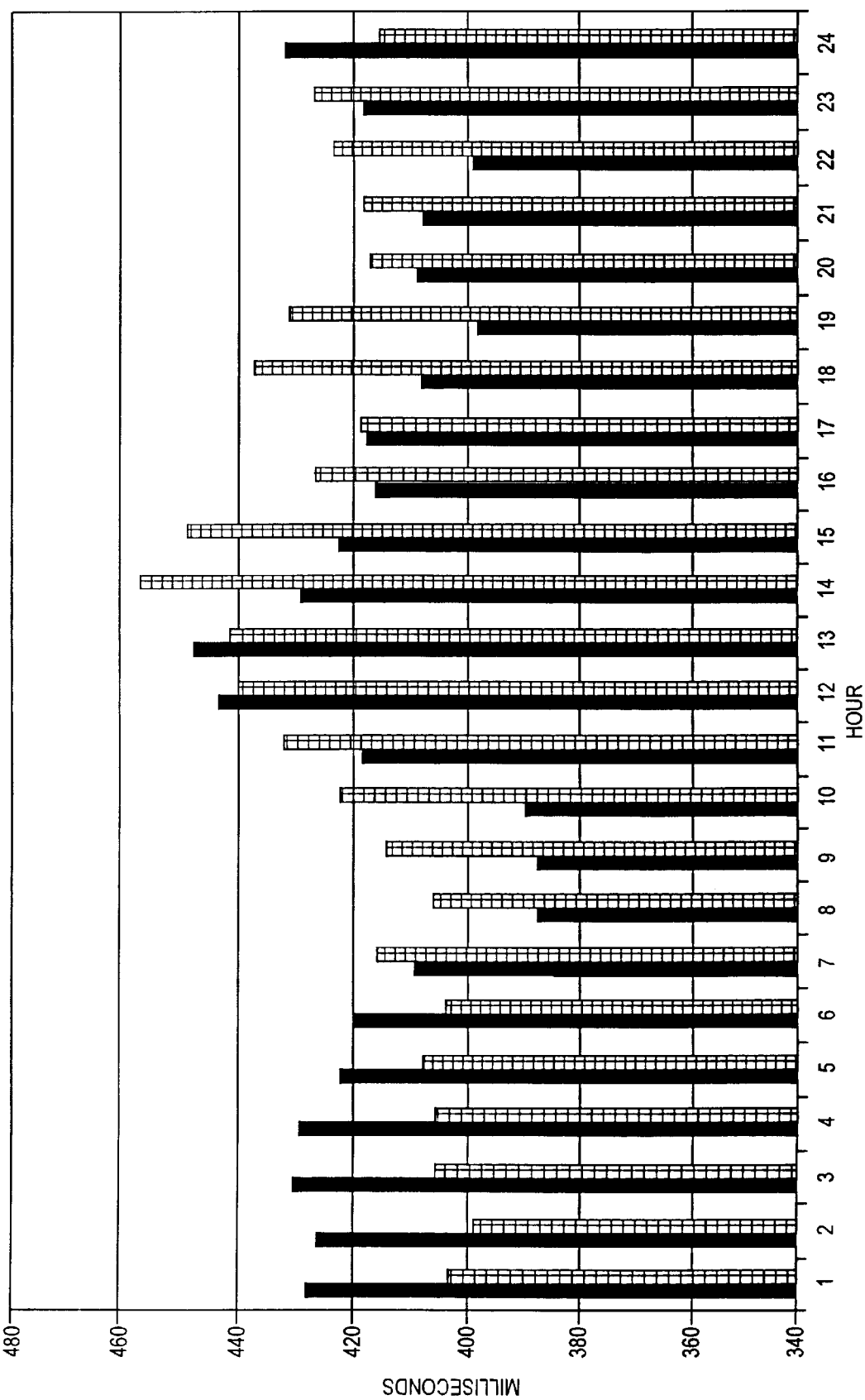
FIG. 12 illustrates an example of average hourly QT and QTc measurements from a peak dose recording (solid=QT, cross-hatched=QTc)

The circadian rhythm of the subject's QT interval measurements was also changed. FIG. 11 shows the average hourly QT and QTc measurements from the baseline recording. FIG. 12 shows the hourly QT and QTc measurements from the peak dose recording. Table 3 shows the day versus night values.

Figure 13:
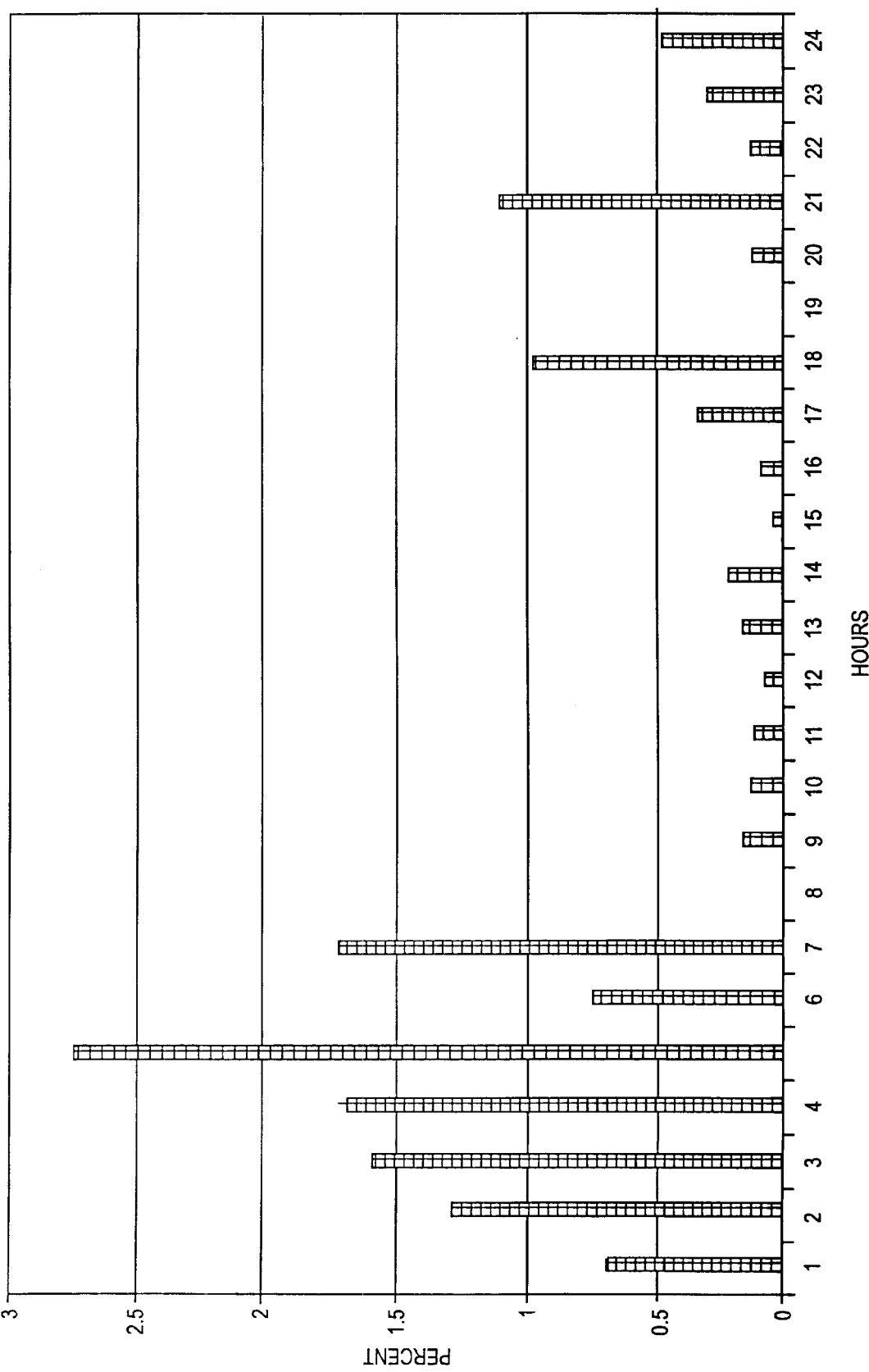
FIG. 13 illustrates an example of hourly values for %QT and %QTc at Baseline (solid=QT, cross-hatched=QTc)
Figure 14:
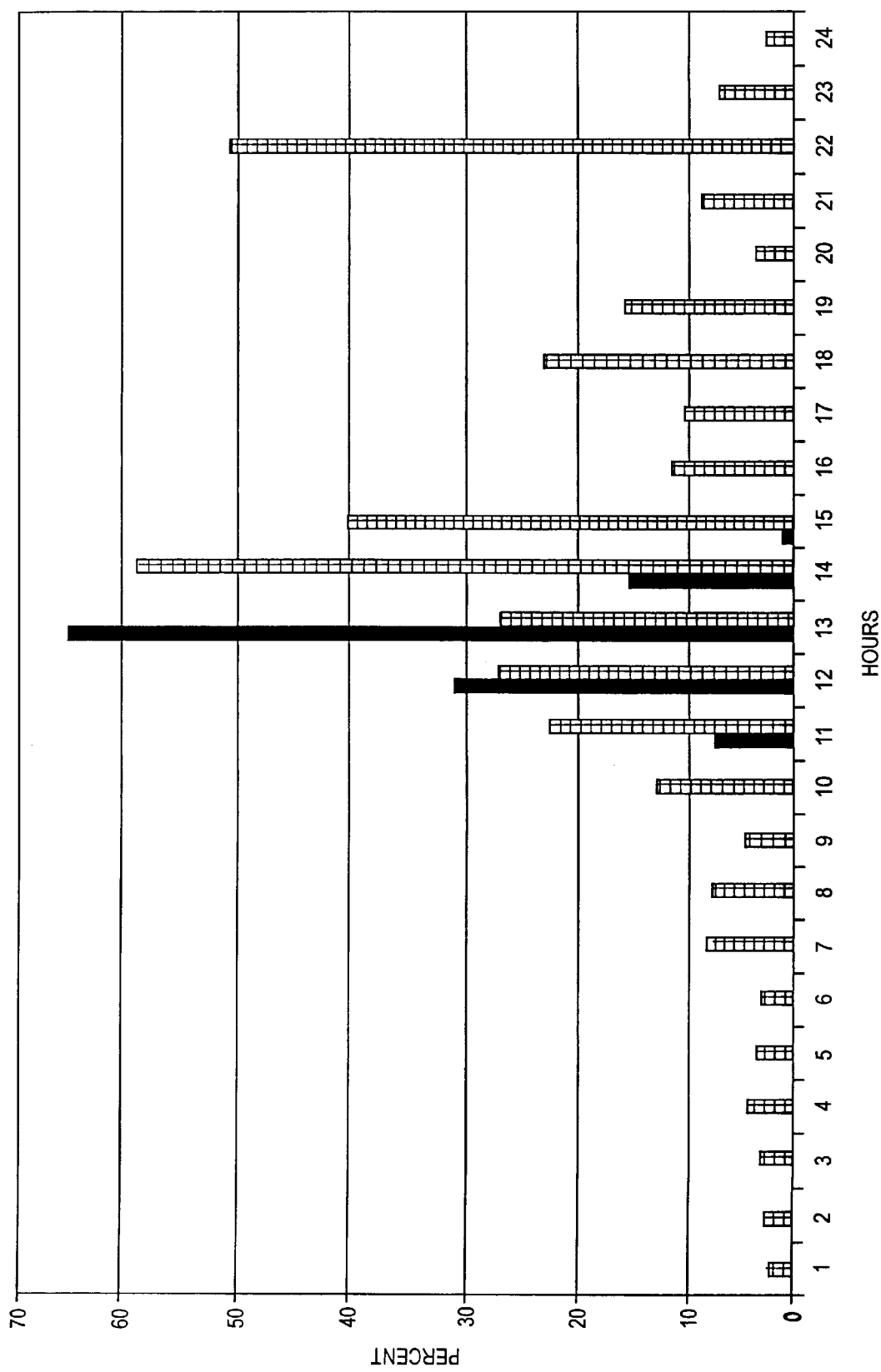
FIG. 14 illustrates an example of hourly values for %QT and %QTc at peak dose (solid=QT, cross-hatched=QTc)

Even with the increase in QT and QTc intervals during the peak dose, the values during nighttime were longer than during the daytime hours (p<0.001, p<0.001, respectively). This was true for the %QT and %QTc as well. FIGS. 13 and 14 show the hourly values for %QT and %QTc, respectively.

EXAMPLE 3—ILQT PATIENT

Data for the QT and QT measurements for an ILQT patient is presented in Table 3. The means for both QT and QTc are considered within normal clinical limits. There was, however, an increase in the %QT and %QTc over the normal subject, and baseline measurements of the drug-study subject.

Figure 15:
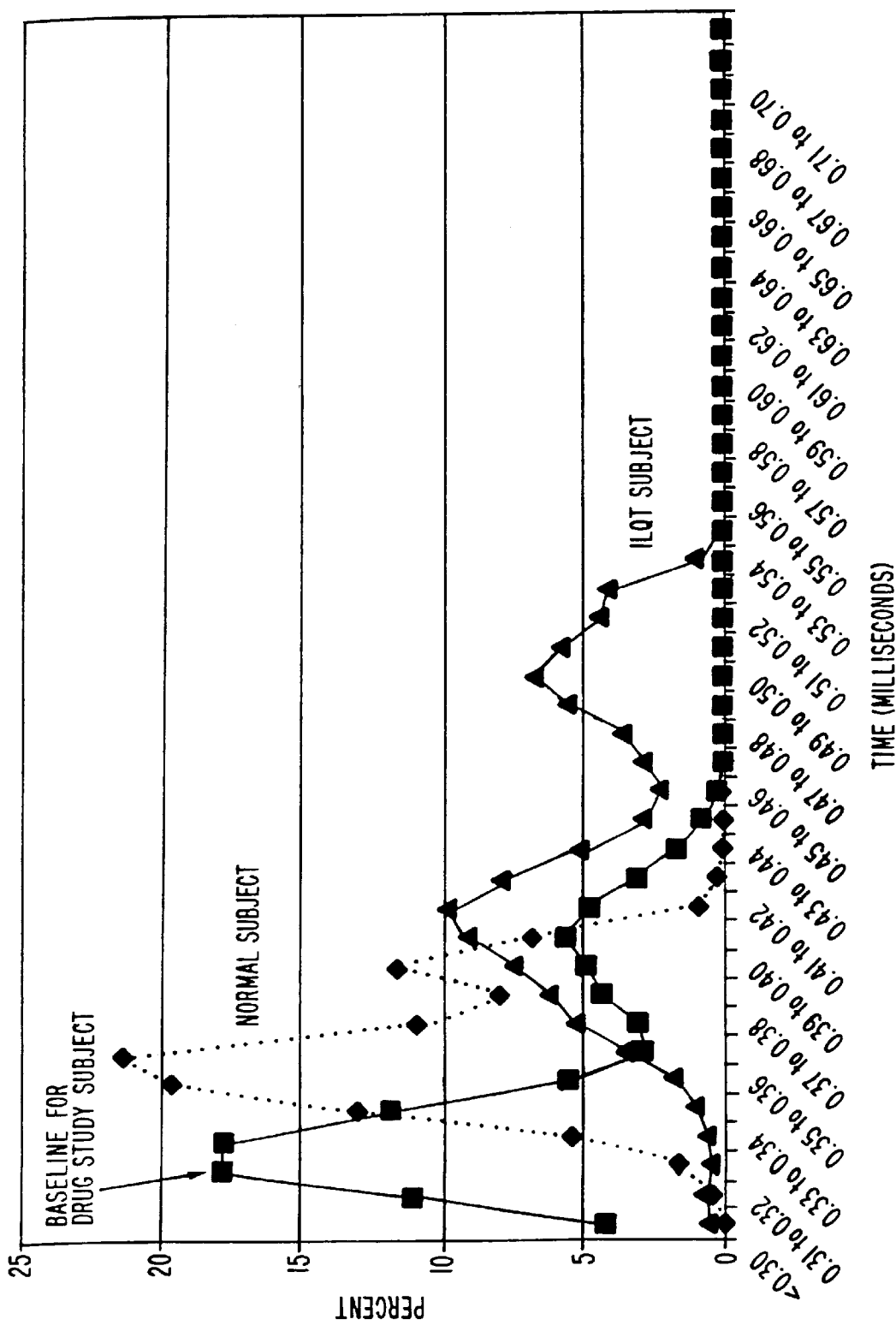
FIG. 15 illustrates an example of comparative histograms of %QT for Normal, Drug Study, and ILQT Subjects
Figure 16:
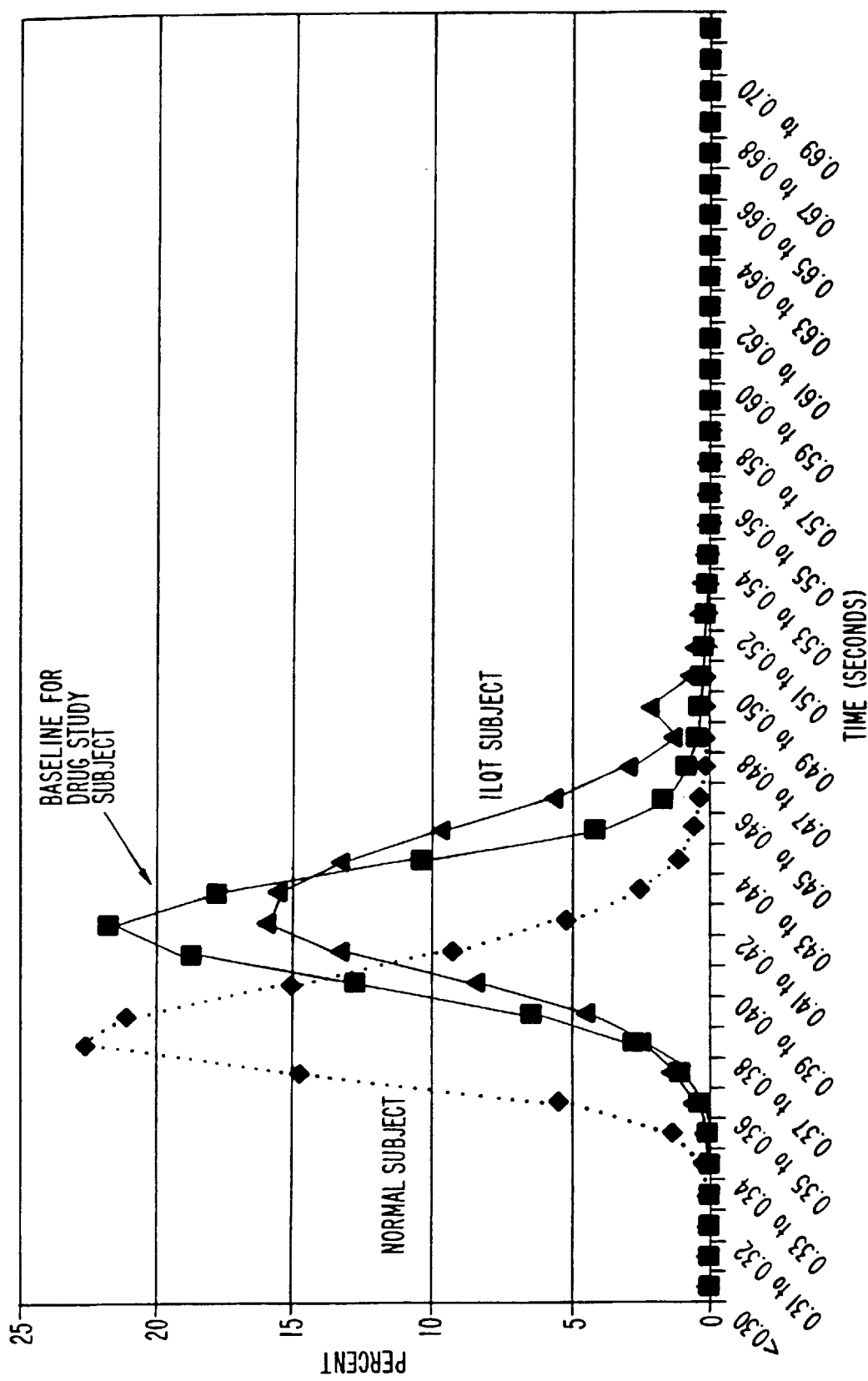
FIG. 16 illustrates an example of comparative histograms of %QTc for Normal, Drug Study, and ILQT Subjects

FIGS. 15 and 16 show comparative histograms of for the three subjects. The %QT is shown in FIG. 15 and the %QTc is shown in FIG. 16. In both histograms, the ILQT subject has a higher percentage of beats greater than 450 ms.

Despite a lack of standardization, it is well understood that patients who have a propensity for the development of ventricular tachycardia sometimes display prolonged QT intervals. Using the present invention, patients with ILQT have displayed more abnormal QT and QTc intervals as assessed by AECG analysis.

In a preferred embodiment, the present invention represents a new method and apparatus for quantifying the QT interval over a period of time. The invention allows a quantitative assessment of the number of beats with QT and QTc intervals of specific lengths. For example, the invention allows identification of the number of cardiac cycles with the QT interval measured at 0.45 to 0.46 seconds. This allows creation of an index that displays the number of cardiac cycles with QT intervals greater than 0.45 seconds.

In addition, this method and apparatus allows the identification of the number of cardiac cycles with QTc measurements greater than 0.45 seconds. Using the present invention, the threshold can be set by the operator. In the particular study described herein, a threshold point out 0.45 seconds was used.

In a preferred embodiment, the method and apparatus may make use of high-speed computer processors, such as the Pentium II processor, and large capacity data-storage media. In a preferred embodiment a 266 mHz Pentium II processor with an 8.6-gigabyte hard drive may be used to analyze and store the large data files.

There is some controversy regarding the use of correction formulas to calculate QTc measurements. While approximately twelve different formula are available for correction of the QT interval, in a preferred embodiment of the present invention Bazett's formula has been used when referring to QTc. The present invention is capable of retaining the raw beat-to-beat variability data regardless of the correction formula used. A preferred embodiment of the computer program allows insertion of other formulas, as knowledge of the dynamic nature of the QT interval improves.

The present invention demonstrates that there is an incidence of prolonged QT and QTc intervals in ostensibly normal subjects. The two normal subjects showed that when considering a 24-hour period, up to 5% of the QTc intervals may exceed 450 milliseconds. Using both 12-lead ECG and 24-hour AECG recordings, others have reported frequent prolonged QT and QTc intervals in normal subjects when looking at random beats. This finding suggests that random observation of the QT interval on the resting 12-lead ECG should be viewed with caution in assessing potential QT and QTc prolongation occurring both spontaneously and with drug therapy. The observation that prolonged QT intervals can occur in normal subjects has led us to develop the %QT and %QTc measurements. These quantitative assessments of the number of beats with various degrees of QT and QTc prolongation are more likely to accurately measure the QT interval on 24-hour AECG recordings than random measurements taken from the resting 12-lead ECG. Further study may be useful to correctly identify dynamic changes in QT and QTc interval measurements in normal subjects stratified by age.

The QT interval has been shown to vary with both heart rate and autonomic function. The applicants have observed that there is a time lag between an increase in heart rate and a subsequent reduction in the length of the QT interval. This lag phase has been reported by others as lasting one minute to three minutes in length. See Franz M R, Swerdlow C D, Liem B L: Cycle-length dependence on human action potential duration in vivo: effects of single extra stimuli, sudden sustained rate acceleration and deceleration, and different steady-state frequencies. J Clin Invest 82:972, 1988; Coumel P, Fayn J, Maison-Blanche P, Rubel P: Clinical relevance of assessing QT dynamicity in Holter recordings. J Electrocardiol 27(suppl):62, 1994. Since the QT interval is under the control of both sodium and potassium channels, this mechanism may vary in terms of time from one individual to another. This time lag may show more variability in subjects with genetic defects in their sodium, potassium, and calcium channels.

Applicants have analyzed more than 80,000 beats per AECG recording to assess variation and dynamic changes in QT and QTc intervals. Applicants data suggest that an automated measurement technique, in addition to being able to process more AECG measurements more quickly, is more reliable than manual measurements of the QT and QTc interval.

Percent QTc measurement in accordance with the present invention allows for a quantitative assessment of the number of beats in a 24-hour AECG recording that exceeds some pre-selected threshold value. In a preferred embodiment of the present invention the applicants used 0.45 seconds as the threshold.

The present invention, in a preferred embodiment, is directed to a method and apparatus for the quantification of beat-to-beat QT and QTc interval measurements from ambulatory electrocardiographic recordings. This method and apparatus tends to be superior to averaging, as it retains the raw beat-to-beat variability that may be useful in calculating a subject's risk of sudden death from ventricular arrhythmias.

Figure 17:
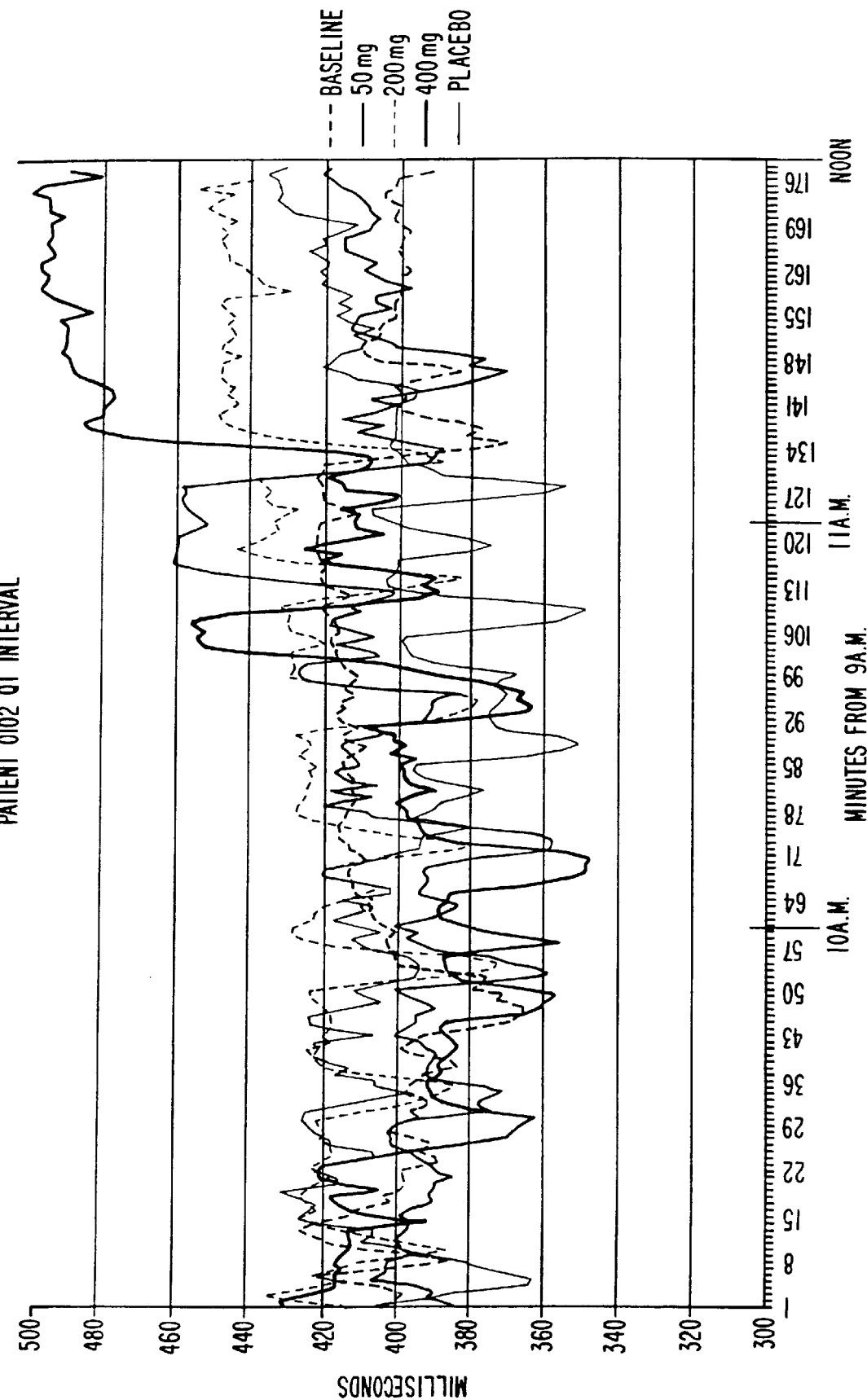
FIG. 17 illustrates an example of five halter monitorings on the same patient being treated with a pharmaceutical.
Figure 18:
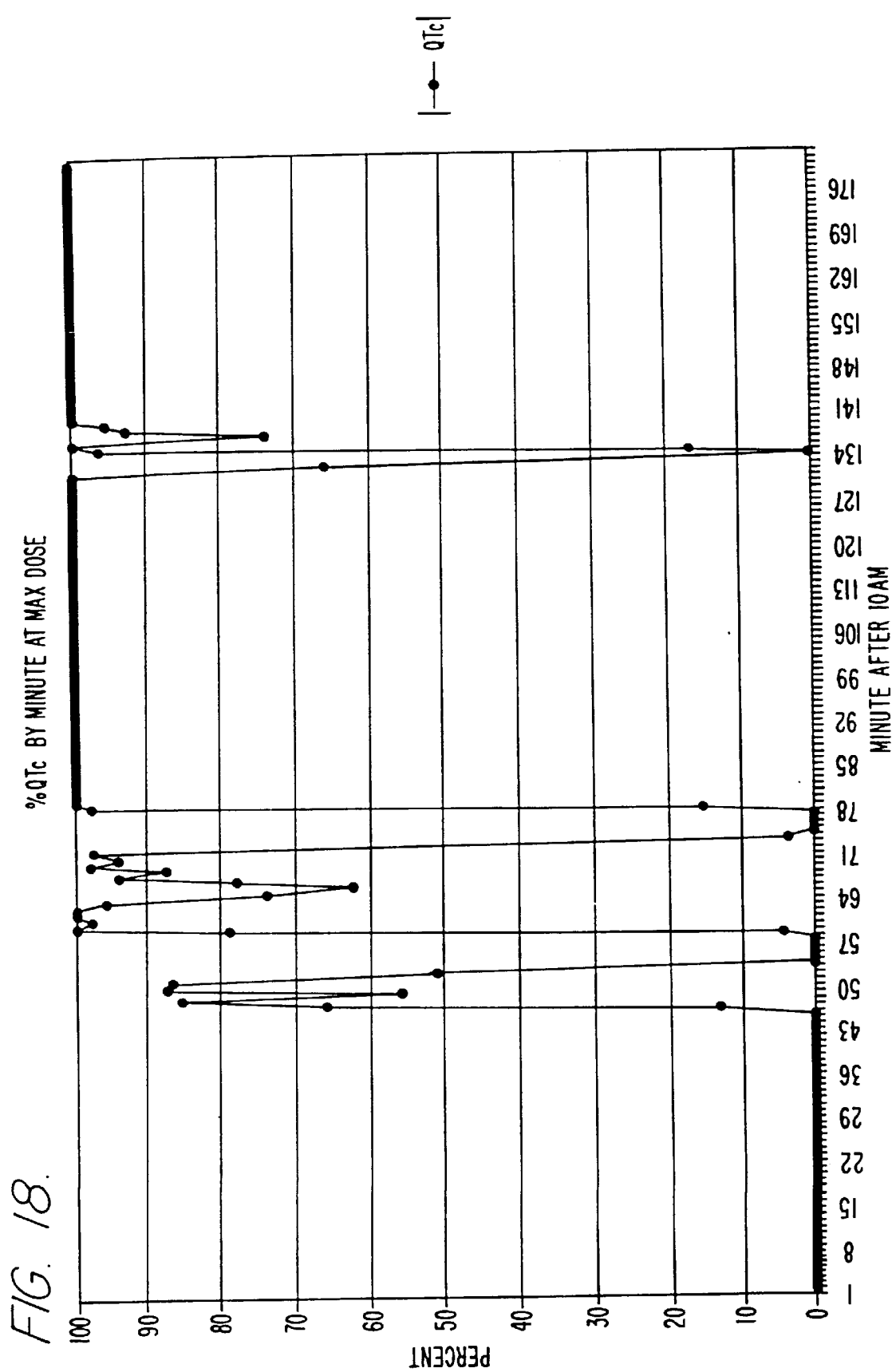
FIG. 18 illustrates an example of the %QT by minute, one hour after maximum dose of a pharmaceutical.
Figure 19:
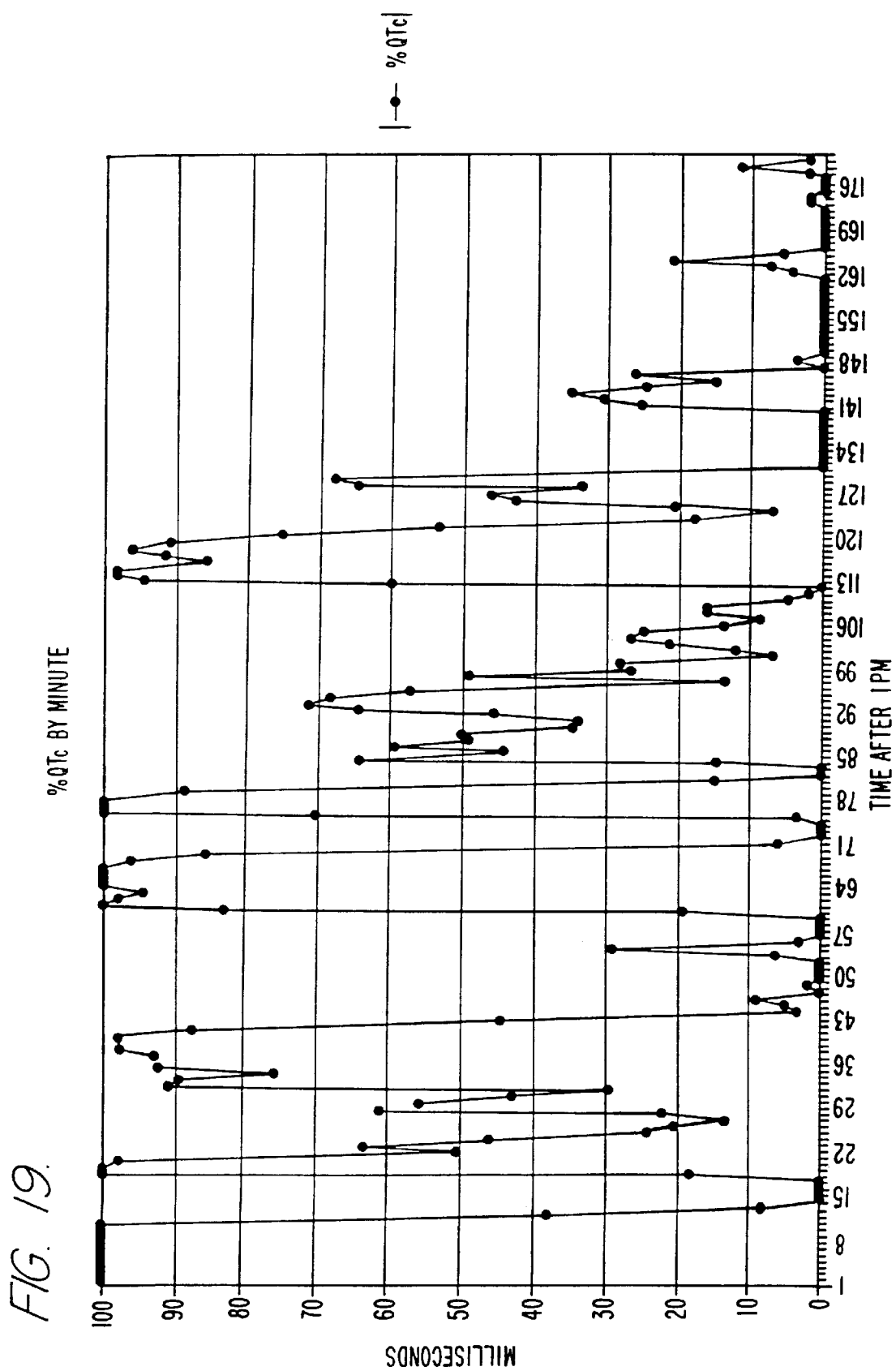
FIG. 19 illustrates an example of the %QT by minute, four hours after maximum dose of a pharmaceutical.

A QT binning technique in accordance with the present invention may be used to provide information about the effects of a pharmaceutical. For instance, in the example illustrated in FIGS. 17–19, a patient had five separate Holter monitorings. The first was a base line monitoring. Then three doses and a placebo were provided to the patient in random order and the patient was monitored. Using a binning method in accordance with the present invention, an increase in the QT interval could be demonstrated better than by simply averaging or just measuring a QT interval. For instance, in the example illustrated in FIGS. 18 and 19, there was no beats greater than 450 milliseconds until about 10:43 AM. The dose was given at about 9:50 AM, so these graphs indicate that it took the dose about one hour to work. Then, after about one hour, the percentage of beats greater than 450 milliseconds increased to between about 80% and about 100% and then dropped off after a number of hours, at about 4:00 PM.

This information indicates that the drug prolonged the QT interval. Using a prior art averaging technique based upon a single measurement, like a 12 lead ECG, if the number of beats or the percentage of beats greater than 450 milliseconds was not 100%, then there would be only a random chance of getting the beats and characterizing the beats properly.

Although the preferred embodiment of the present invention has been described herein with respect to measurement and analysis of the QT interval, it will be recognized that a method and apparatus in accordance with the present invention may also be useful in the measurement and analysis of a wide variety of other ECG and related biologically significant intervals. For example, with reference to the examples of ECG fiducial points illustrated in FIG. 3, the present invention may be useful for the measurement and analysis of, without limitation, the PR interval, the RR interval, the QT interval, the ST interval, the QRS duration, the JT interval, the QTA apex, and the interval between P beginning and P end.

In a preferred embodiment, the method takes discreet measurements and discreet intervals and places them into a time series bin or an amplitude series bin. For example, all of the PR intervals in a sample could be selected and coded according to their length and then put them into bins. Each bin could be characterized by a frequency. The same analysis could be performed using an RR interval, or a QT interval.

With an ST interval it may be preferable to use an amplitude series bin rather than a time series bin. An ST may be depressed or elevated relative to base line. That depression or elevation may be measured and put into amplitude bins.

The presently disclosed embodiments are to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. A quantitative method of measuring a cardiac function interval, the method comprising:
   collecting, over an extended period of time, beat-to-beat data representative of a cardiac interval, each beat-to-beat data having a value,
   defining a plurality of bins, each one of the plurality of bins having a defined value range,
   organizing each of the collected data into one of the plurality of bins in accordance with the value of the data and the value range of the bin, and
   calculating a percentage of data in each bin based upon the quantity of data in each bin.

2. The method of claim 1 wherein the step of calculating comprises calculating a percentage of data exceeding a defined threshold.

3. The method of claim 2 wherein the defined threshold comprises a time threshold.

4. The method of claim 2 wherein the threshold comprises an amplitude threshold.

5. The method of claim 1 wherein the step of collecting data comprises obtaining an ambulatory electrocardiographic monitoring recording.

6. The method of claim 1 wherein the cardiac function interval comprises at least one of a QT interval, a QTc interval, a PR interval, an RR interval, an ST interval, a QRS duration, a JT interval, a QTA apex, and an interval between P beginning and P end.

7. A device for quantitatively measuring a cardiac function interval, the device comprising:
   means for collecting, over an extended period of time, beat-to-beat data representative of a cardiac interval, each beat-to-beat data having a value,
   means for defining a plurality of bins, each one of the plurality of bins having a defined value range,
   means for organizing each of the collected data into one of the plurality of bins in accordance with the value of the data and the value range of the bin, and
   means for calculating a percentage of data in each bin based upon the quantity of data in each bin.

8. The device of claim 7 wherein the means for calculating comprises means for calculating a percentage of data exceeding a defined threshold.

9. The device of claim 8 wherein the defined threshold comprises a time threshold.

10. The device of claim 8 wherein the threshold comprises an amplitude threshold.

11. The device of claim 7 wherein the means for collecting data comprises ambulatory electrocardiographic monitor.

12. The device of claim 7 wherein the cardiac function interval comprises at least one of a QT interval, a QTc interval, a PR interval, an RR interval, an ST interval, a QRS duration, a JT interval, a QTA apex, and an interval between P beginning and P end.

13. A method of measuring an effect of a pharmaceutical on a subject, comprising:
   providing a pharmaceutical to the subject,
   collecting, over an extended period of time, beat-to-beat data representative of a cardiac interval of the subject, each beat-to-beat data having a value,
   defining a plurality of bins, each one of the plurality of bins having a defined value range, organizing each of the collected data into one of the plurality of bins in accordance with the value of the data and the value range of the bin, and calculating a percentage of data in each bin based upon the quantity of data in each bin.

14. A quantitative method of measuring a cardiac function interval, the method comprising:

collecting, over an extended period of time, beat-to-beat data representative of a cardiac interval, each beat-to-beat data having a value, stratifying the collected data, based upon the value of the collected data, in accordance with a plurality of defined bins, each one of the plurality of bins having a defined value range, and calculating a percentage of data in each bin based upon the quantity of data in each bin.

15. A device for quantitatively measuring a cardiac function interval, the device comprising:

means for collecting, over an extended period of time, beat-to-beat data representative of a cardiac interval, each beat-to-beat data having a value, means for stratifying the collected data, based upon the value of the collected data, in accordance with a plurality of defined bins, each one of the plurality of bins having a defined value range, and means for calculating a percentage of data in each bin based upon the quantity of data in each bin.

* * * * *